(12) United States Patent
Chin et al.

(10) Patent No.: US 9,840,555 B2
(45) Date of Patent: Dec. 12, 2017

(54) METHOD FOR PRODUCING HUMAN MONOCLONAL ANTIBODIES THAT BINDS TO AT LEAST ONE PART OF HMGB1

(71) Applicants: Li-Te Chin, Hsinchu (TW); Shu-Ching Hsu, Kaohsiung County (TW); Kai-Chen Wang, Taipei (TW)

(72) Inventors: Li-Te Chin, Hsinchu (TW); Shu-Ching Hsu, Kaohsiung County (TW); Kai-Chen Wang, Taipei (TW)

( * ) Notice: Subject to any disclaimer, the term of this patent is extended or adjusted under 35 U.S.C. 154(b) by 324 days.

(21) Appl. No.: 14/526,842

(22) Filed: Oct. 29, 2014

(65) Prior Publication Data

US 2015/0126714 A1 May 7, 2015

Related U.S. Application Data

(60) Provisional application No. 61/899,473, filed on Nov. 4, 2013.

(51) Int. Cl.
| | | |
|---|---|---|
| C07K 16/18 | (2006.01) | |
| C07K 16/24 | (2006.01) | |
| A61K 39/00 | (2006.01) | |

(52) U.S. Cl.
CPC ........ *C07K 16/24* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,652,138 A | 7/1997 | Burton et al. |
| 5,885,793 A | 3/1999 | Griffiths et al. |
| 6,075,181 A | 6/2000 | Kucherlapati et al. |
| 6,228,361 B1 | 5/2001 | Posner |
| 6,468,533 B1 | 10/2002 | Tracey et al. |
| 7,288,250 B2 | 10/2007 | Newman et al. |
| 7,494,779 B2 | 2/2009 | Chin et al. |
| 8,021,860 B2 | 9/2011 | Chin et al. |
| 8,158,386 B2 | 4/2012 | Chin et al. |
| 2005/0014230 A1* | 1/2005 | Chin ............. C07K 16/00 435/70.21 |
| 2006/0099207 A1* | 5/2006 | Wu ............... C07K 16/24 424/133.1 |
| 2008/0113385 A1* | 5/2008 | Newman ........ C07K 14/4718 435/7.1 |

FOREIGN PATENT DOCUMENTS

| | | |
|---|---|---|
| WO | 9201047 A | 1/1992 |
| WO | 2010104828 A | 9/2010 |

OTHER PUBLICATIONS

Lederman et al., Molecular Immunology 28: 1171-1181 (1991).*
Li et al., PNAS 77: 3211-3214 (1980).*
Edward Abraham, John Arcaroli, Aaron Carmody, Haichao Wang and Kevin J. Tracey, Cutting Edge: HMG-1 as a Mediator of Acute Lung Inflammation, The Journal of Immunology 2000;165: 2950-2954.
Ulf Andersson, Haichao Wang, Karin Palmblad, Ann-Charlotte Aveberger, Ona Bloom, Helena Erlandsson-Harris, Alfred Janson, Riikka Kokkola, Minghuang Zhang, Huan Yang, and Kevin J.Tracey, High Mobility Group 1 Protein (HMG-1) Stimulates Proinflammatory Cytokine Synthesis in Human Monocytes, J. Exp. Med,vol. 192, No. 4, Aug. 21, 2000, pp. 565-570.
Marco E. Bianchi, Angelo A. Manfredi, High-mobility group box 1 (HMGB1) protein at the crossroads between innate and adaptive immunity, Immunological Reviews 2007, vol. 220, pp. 35-46.
Tiziana Bonaldi, Fabio Talamo, Paola Scaffidi, Denise Ferrera, Annalisa Porto, Angela Bachi, Anna Rubartelli, Alessandra, Agresti and Marco E. Bianchi, Monocytic cells hyperacetylate chromatin protein HMGB1 to redirect it towards secretion, The EMBO Journal, vol. 22, pp. 5551-5560, 2003.
Viroj Boonyaratanakornkit, Vida Melvin, Paul Prendergast, Magda Altmann, Lorenza Ronfani, Marco E. Bianchi, Laima Taraseviciene, Steven K. Nordeen, Elizabeth A. Allegretto and Dean P. Edwards, High-Mobility Group Chromatin Proteins 1 and 2 Functionally Interact with Steroid Hormone Receptors to Enhance Their DNA Binding in Vitro and Transcriptional Activity in Mammalian Cells, Mol.Cell. Biol.1998, 18 (8), 4471.
Michael P. Cancro, Peripheral B-cell maturation: the intersection of selection and homeostasis, Immunological Reviewa 2004,vol. 197: 89-101.
Jean Chatellier, Marc H. V. Van Regenmortel, Thierry Vernet and Daniele Altschuh, Functional Mapping of Conserved Residues Located at the VL and VH Domain Interface of a Fab, J. Mol. Biol. (1996) 264, pp. 1-6.
Li-Te Chin, Chishih Chu, Han-Min Chen, Shu-Ching Hsu, Bor-Chun Weng and Chi-Hong Chu, Site-directed in vitro immunization leads to a complete human monoclonal IgG4 lambda that binds specifically to the CDR2 region of CTLA-4 (CD152) without interfering the engagement of natural ligands, BMC Biotechnology 2007, pp. 1-12.
Li-Te Chin, Jyh-Young Cheng, Shih-Chien Lu, Andrew Cheng-Hsiang Chang, Chi-Hong Chu, Ching-Liang Meng, Establishment and Evaluation of Mouse-Human Heteromyeloma Cell Lines Obtained by Electrofusion for Immortalizing Human Immunoglobulins, J Biomed Lab Sci 2001 vol. 13 No. 4, pp. 117-123.
Daniela Baumann Cornelio, Regina Pedrini Braga, Marcos Wengrover Rosa, Antonio Celso Ayub, Devic's neuromyelitis optica and pregnancy: distinction from multiple sclerosis is essential, Arch Gynecol Obstet (2009) 280:475-477.
Anne S. De Groot and David W. Scott, Immunogenicity of protein therapeutics, Trends in Immunology, vol. 28 No. 11.
R.K. Dore, S. Mathews, J. Schechtman, W. Surbeck, D. Mandel, A. Patel, L. Zhou, P. Peloso, The immunogenicity, safety, and efficacy of etanercept liquid administered once weekly in patients with rheumatoid arthritis, Clinical and Experimental Rheumatology 2007; 25: 40-46.
A. Farrugia and P. Poulis, Intravenous immunoglobulin: regulatory perspectives on use and supply, Transfusion Medicine, 2011,11, pp. 63-74.
Mitchell P Fink, Bench-to-bedside review: High-mobility group box 1 and critical illness, Critical Care 2007, 11: 229, pp. 1-8.
Carmen Fiuza, Michael Bustin, Shefali Talwar, Margaret Tropea, Eric Gerstenberger, James H. Shelhamer and Anthony F. Suffredini, Inflammation-promoting activity of HMGB1 on human microvascular endothelial cells, Blood 2003 101: 2652-2660.

(Continued)

*Primary Examiner* — Phillip Gambel
(74) *Attorney, Agent, or Firm* — Bacon & Thomas, PLLC (57) ABSTRACT

The present invention relates to methods of making human anti-HMGB1 antibodies, compositions comprising these antibodies and methods of using the antibodies and compositions in HMGB1 associated-neuropathy.

1 Claim, 4 Drawing Sheets

(56) References Cited

OTHER PUBLICATIONS

Vladka Gaberc-Porekar and Viktor Menart, Potential for Using Histidine Tags in Purification of Proteins at Large Scale, Chem Eng. Technol. 2005, 28, No. 11, pp. 1306-1314.
Graham H. Goodwin, Clive Sanders, and Ernest W. Johns, A new group of chromatin-associated proteins with a high content of acidic and basic amino acids, Eur. J. Biochem. 38, 14-19 (1973).
Robert Hock, Takashi Furusawa,Tetsuya Ueda and Michael Bustin, HMG chromosomal proteins in development and disease, Trends in Cell Biology vol. 17 No. 2.
Osamu Hori, Jerold Brett, Timothy Slattery, Rong Cao, Jinghua Zhang, Jing Xian Chen, Mariko Nagashima, Erik R. Lundh, Sharmila Vijay, Di Nitecki, John Morser, David Stern and Ann Marie Schmidt, The Receptor for Advanced Glycation End Products (RAGE) is a Cellular Binding Site for Amphoterin. Mediation of Neurite Outgrowth and Co-Expression of RAGE and Amphoterin in the Developing Nervous System, J. Biol Chem. 1995, 270: 25752-25761.
Henri J. Huttunen, Carole Fages and Heikki Rauvala, Receptor for Advanced Glycation End Products (RAGE)-mediated Neurite Outgrowth and Activation of NF-kappaB Require the Cytoplasmic Domain of the Receptor but Different Downstream Signaling Pathways, J. Biol. Chem. 1999, 274:19919-19924.
Paul Imbach, 30 years of immunomodulation by intravenous immunoglobulin, Immunotherapy 2012 4(7), 651-654.
Paul Imbach, Treatment of immune thrombocytopenia with intravenous immunoglobulin and insights for other diseases, Swiss Med Wkly. 2012; 142: w13593, pp. 1-10.
Ian R. Mackay, M. D., and Fred S. Rosen, M. D., Immunomodulation of Autoimmune and Inflammatory Diseases With Intravenous Immune Globulin, N Engl J Med, vol. 345, No. 10, 2001, pp. 747-755.
Jurgen A. Kleinschmidt, Ulrich Scheer, Marie-Christine Dabauvalle, Michael Bustin, and Werner W. Franke, High Mobility Group Proteins of Amphibian Oocytes: A Large Storage Pool of a Soluble High Mobility Group-1-like Protein and Involvement in Transcriptional Events, The Journal of Cell Biology, vol. 97, 1983, pp. 838-848.
Real Lemieux, Renee Bazin, Sonia Neron, Therapeutic intravenous immunoglobulins, Molecular Immunology 42 (2005) 839-48.
Keyue Liu, Shuji Mori, Hideo K Takahashi, Yasuko Tomono, Hidenori Wake, Toru Kanke, Yasuharu Sato, Norihito Hiraga, Naoto Adachi, Tadashi Yoshino, and Masahiro Nishibori, Anti-high mobility group box 1 monoclonal antibody ameliorates brain infarction induced by transient ischemia in rats, FASEB J. 21, 3904-3916 (2007).
Roberta Palumbo, Maurilio Sampaolesi, Francesco De Marchis, Rossana Tonlorenzi, Sara Colombetti, Anna Mondino, Giulio Cossu, and Marco E. Bianchi, Extracellular HMGB1, a signal of tissue damage, induces mesoangioblast migration and proliferation, The Journal of Cell Biology, vol. 164, Nov. 3, Feb. 2, 2004, pp. 441-449.
Jong Sung Park, Daiva Svetkauskaite, Qianbin He, Jae-Yeol Kim, Derek Strassheim, Akitoshi Ishizaka and Edward Abraham, Involvement of Toll-Like Receptors 2 and 4 in Cellular Activation by High Mobility Group Box 1 Protein, J. Biol. Chem. 2004, 279: 7370-7377.
Jean-Francois Seite, Yehuda Shoenfeld, Pierre Youinou, Sophie Hillion, What is the contents of the magic draft IVIg? Autoimmunity Reviews 7 (2008) 435-439.
Wang, H., Bloom, O., Zhang, M., Vishnubhakat, J.M., Ombrellino, M., Che, J., Frazier, A., Yang, H., Ivanova, S., Borovikova, L., Manogue, K.R., Faist, E., Abraham, E., Andersson, J., Andersson, U., Molina, P.E., Abumrad, N.N., Sama, A. and Tracey, K.J, HMG-1 as a Late Mediator of Endotoxin Lethality in Mice, Science 285, pp. 248-251. (1999).
Haichao Wang, Huan Yang, Christopher J Czura, Andrew E Sama, and Kevin J. Tracey, HMGB1 as a Late Mediator of Lethal Systemic Inflammation, Am J Respir Crit Care Med, vol. 164, pp. 1768-1773, 2001.
K.-C. Wang, C.-P. Tsai, C.-L. Lee, S.-Y. Chen, L.-T. Chin and S.-J. Chen, Elevated Plasma High-Mobility Group Box 1 Protein Is a Potential Marker for Neuromyelitis Optica, Neuroscience 226 (2012) pp. 510-516.
Matthias Wittstock, Reiner Benecke, Uwe K. Zettl, Therapy with Intravenous Immunoglobulins: Complications and Side-Effects, Eur Neurol 2003; 50;172-175.
Runkuan Yang, Tomoyuki Harada, Kevin P Mollen, Jose M Prince, Ryan M Levy, Joshua A Englert, Margot Gallowitsch-Puerta, Lihong Yang, Huan Yang, Kevin J Tracey, Brian G Harbrecht, Timothy R Billiar, and Mitchell P Fink, Anti-HMGB1 Neutralizing Antibody Ameliorates Gut Barrier Dysfunction and Improves Survival after Hemorrhagic Shock, Mol Med 12, (4-6)105-114, 2006.

* cited by examiner

```
                        SEQUENCE LISTING

<160> NUMBER OF SEQ ID NOS: 6

<210> SEQ ID NO 1
<211> LENGTH: 215
<212> TYPE: PRT
<213> ORGANISM: Homo sapiens
<220> FEATURE:
<221> NAME/KEY: PEPTIDE
<222> LOCATION: (1)..(215)

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Asp
```

-continued

```
<210> SEQ ID NO 2
<211> LENGTH: 15
<212> TYPE: PRT
<213> ORGANISM: Clostridium tetani
<220> FEATURE:
<221> NAME/KEY: PEPTIDE
<222> LOCATION: (1)..(15)
<300> PUBLICATION INFORMATION:
<301> AUTHORS: Demotz S, Lanzavecchia A, Eisel U, Niemann H, Widmann C,
      and Corradin G.
<302> TITLE: Delineation of several DR-restricted tetanus toxin T cell
      epitopes
<303> JOURNAL: Journal of Immunology
<304> VOLUME: 142
<306> PAGES: 394-402
<307> DATE: 1989-01-15
<313> RELEVANT RESIDUES IN SEQ ID NO: (1)..(15)

<400> SEQUENCE: 2

Gln Tyr Ile Lys Ala Asn Ser Lys Phe Ile Gly Ile Thr Glu Leu
1               5                   10                  15

<210> SEQ ID NO 3
<211> LENGTH: 12
<212> TYPE: PRT
<213> ORGANISM: Homo sapiens
<220> FEATURE:
<221> NAME/KEY: PEPTIDE
<222> LOCATION: (1)..(12)

<400> SEQUENCE: 3

Asp Lys Ala Arg Tyr Glu Arg Glu Met Lys Thr Tyr
1               5                   10

<210> SEQ ID NO 4
<211> LENGTH: 12
<212> TYPE: PRT
<213> ORGANISM: Homo sapiens
<220> FEATURE:
<221> NAME/KEY: PEPTIDE
<222> LOCATION: (1)..(12)

<400> SEQUENCE: 4

Lys Asp Ile Ala Ala Tyr Arg Ala Lys Gly Lys Pro
1               5                   10

<210> SEQ ID NO 5
<211> LENGTH: 27
<212> TYPE: PRT
<213> ORGANISM: Artificial Sequence
<220> FEATURE:
<223> OTHER INFORMATION: HMG A box peptides were synthesized and used to
      prepare combined epitopes in conjugation with sequence derived
      from the tetanus toxin
<220> FEATURE:
<221> NAME/KEY: PEPTIDE
<222> LOCATION: (1)..(27)

<400> SEQUENCE: 5

Gln Tyr Ile Lys Ala Asn Ser Lys Phe Ile Gly Ile Thr Glu Leu Asp
1               5                   10                  15

Lys Ala Arg Tyr Glu Arg Glu Met Lys Thr Tyr
            20                  25

<210> SEQ ID NO 6
<211> LENGTH: 27
<212> TYPE: PRT
```

-continued

```
<213> ORGANISM: Artificial Sequence
<220> FEATURE:
<223> OTHER INFORMATION: RAGE peptides were synthesized and used to
      prepare combined epitopes in conjugation with sequence derived
      from the tetanus toxin
<220> FEATURE:
<221> NAME/KEY: PEPTIDE
<222> LOCATION: (1)..(27)

<400> SEQUENCE: 6

Gln Tyr Ile Lys Ala Asn Ser Lys Phe Ile Gly Ile Thr Glu Leu Lys
1               5                   10                  15

Asp Ile Ala Ala Tyr Arg Ala Lys Gly Lys Pro
            20                  25
```

METHOD FOR PRODUCING HUMAN MONOCLONAL ANTIBODIES THAT BINDS TO AT LEAST ONE PART OF HMGB1

CROSS REFERENCE TO RELATED APPLICATION

This application claims the benefit of filing date of U.S. Provisional Application Ser. No. 61/899,473, entitled "Complete human neutralizing antibody for high mobility group box 1 (HMGB1)-associated neuromyelitis" filed Nov. 4, 2013, the entire contents of which are specifically incorporated herein by reference.

BACKGROUND OF THE INVENTION

1. Field of the Invention

The present invention relates to neutralizing antibodies targeting high mobility group box 1 (HMGB1), and compositions and methods comprising such antibodies useful in treating, inhibiting or preventing HMGB1-associated neuropathy. The invention also relates to the combination of the variable regions of heavy and light chain immunoglobulins derived from a single human antibody-producing cell and amino acid molecules encoding such antibodies and antigen-binding portions, methods of making human anti-HMGB1 antibodies and antigen-binding portions, compositions comprising these antibodies and antigen-binding portions and methods of using the antibodies, antigen-binding portions, and compositions.

2. Description of Related Art

In normal physiological conditions, HMGB1 is confined to the nucleus as a non-histone DNA binding protein that is involved in regulation of chromatin dynamics (Hock et al., 2007), such as stabilizing nucleosome formation (Goodwin et al., 1973), facilitating gene transcription (Kleinschmidt et al., 1983) and modulating steroid hormone receptors (Boonyaratanakornkit et al., 1998). In contrast, in the case of tissue injury, HMGB1 migrates toward the cytoplasm and then is released extracellularly, acting as a danger signal (Bianchi and Manfredi, 2007). In addition to being passively released by necrotic cells, HMGB1 can also be actively secreted by specific cells, e.g., macrophages and myeloid cells, of the innate immune system activated by pro-inflammatory signals such as lipopolysaccharide, tumor necrosis factor-α (TNF-α) and interleukin-1 β(IL1-β) (Bonaldi et al., 2003). It has been also demonstrated as a cytokine that mediates endotoxin lethality (Wang et al., 1999), propagating inflammation (Wang et al., 2001), prolonging macrophage activation (Andersson et al., 2000) and chemoattracting mesoangioblast (Palumbo et al., 2004). It is becoming increasingly clear that both passively released and actively secreted extracellular HMGB1 convey the same danger signal to attract and activate inflammatory cells (Abraham et al., 2000; Andersson et al., 2000), to enhance the expression of cell adhesion molecules in endothelial cells (Fiuza et al., 2003) and to impair the barrier function of endothelium (Yang et al., 2006). Specifically, serum levels of HMGB1 have been directly associated with mortality in patients with lethal sepsis and in experimental models of endotoxaemia (Wang et al., 1999; Fink, 2007), suggesting that HMGB1 is a crucial late mediator of the sustained activation of pro-inflammatory cascades associated with fatal outcomes. Specific receptors interacting with extracellular HMGB1 include receptor for advanced glycation end products (RAGE), toll-like receptor (TLR)-2 and TLR-4 (Hori et al., 1995; Park et al., 2004). The binding of HMGB1 to its receptors results in the activation of several kinases such as extracellular signal-regulated kinases (ERK)-1/2, p38 mitogen-activated protein (MAP) kinases, and c-Jun NH2-terminal kinase, which ultimately leads to the activation of nuclear factor-κB (NF-κB)-dependent genes (Huttunen et al., 1999; Fiuza et al., 2003).

As human HMGB1 has cytokine activities and mediates prolonged systematic inflammation as well as immune responses, we have thus investigated and successfully established the link between an aberrant production of HMGB1 in plasma of patients with neuromyelitis, i.e., neuromyelitis optica (NMO) and conventional multiple sclerosis (MS) (Wang et al., 2012). NMO and MS are a chronic, inflammatory, demyelinating disease of the central nervous system (CNS), most frequently starting with a series of bouts, each followed by complete remission and then a secondary, progressive phase during which the neurological deficit increases steadily. However, the clinical course of NMO is usually more severe than classical or conventional MS (Cornelio et al., 2009). Within five years of onset, fifty percent of NMO patients either loss of functional vision in at least one eye or becoming unable to walk unassisted, or the annual costs for hospitalization exceed several hundred million. There remains an urgent need for prophylactic, pre-emptive and treatment strategies for management of HMGB1-associated neuromyelitis.

Anti-huHMGB1 therapies by using of monoclonal antibodies (mAbs) to specifically bind to and neutralize this particular target protein are expected to be effective in nature. Accordingly, targets with highly selective late mediator are preferred to broaden the therapeutic window (Wang et al., 1999). Furthermore, given the remarkable divergent emergence of the physiological from pathological conditions of huHMGB1, mAbs raised against it are expected to selectively target extracellular HMGB1. Based on these considerations, a monoclonal antibody against huHMGB1 that may inhibit receptor interaction and therefore block kinase activation and the downstream pro-inflammatory response, e.g., TNF-α secretion is highly desirable.

Although mAbs are long-established as essential research tools, their therapeutic promise has taken considerably longer to realize, requiring further advances, such as the humanization of mouse antibodies and/or transgenic protocols, to reduce their immunogenicity inherent in murine proteins. The biopharmaceutical industry has thus seen a full shift of new antibody therapeutics from chimeric to humanized to fully-human sequences. The ultimate objective in the industry is to manufacture a mAb drug that is identical to that which is produced in the human body.

In theory, heavy and light chain components derived entirely from the human origin could be used to assemble mAbs. Indeed, the use of phage antibody technology to construct human heavy and light chain libraries as described in e.g., WO92/01047, U.S. Pat. Nos. 5,652,138 and 5,885,793A, offers the ability to isolate such human antibodies directly. Moreover, U.S. Pat. Nos. 5,652,138 and 6,075,181 demonstrate the feasibility to construct in vivo transgenes to introduce into a non-human animal substantially the entire human immunoglobulin loci and subsequently perform animal immunization to obtain heavy-and-light-chain pairs comprised human sequences. However, the resultant pairings may not be naturally-occurring and still remain to be immunogenic as indicated in the official FDA labeling information (http://www.accessdata.fda.gov)—the frequencies of patient to generate anti-drug antibodies can be as high as 26% and 3.8% for Humira (adalimumab) and Vectibix (panitumumab), respectively. Therefore, this may not be the best available strategy. In fact, while there are general rules (De Groot and Scott, 2007), predicting the precise immunogenicity of a specific protein in the genetically heterogeneous human population is a difficult if not a fundamentally impossible task. This is highlighted again by the case of Enbrel (etanercept), which is a biopharmaceutical produced by recombinant fusion between the TNF receptor and the constant region of the IgG1 antibody to act as a TNF inhibitor. Since both fusion partners are bona fide naturally-occurring ubiquitous proteins in humans and, in principle, should not be immunogenic. Yet clinical data specify that 5.6% treated patients tested positive for anti-etanercept antibodies (Dore et al., 2007).

Our understanding in all of the area of immunogenicity is increasing, but currently it seems impossible to close the circle. Alternatively, a sharp clinical contrast provided by the therapeutic immunoglobulin preparations, and especially intravenous immunoglobulin (IVIg), may well turn out to be optimistic in resolving the problem of immunogenicity. The IVIg refers to a therapeutic biological product containing human IgG that is prepared by large-scale industrial fractionation of human plasma derive from samples collected from thousands of blood donors (Kazatchkine and Kaveri, 2001; Seite et al., 2008), and thus represents in essence a preparation of human polyclonal antibodies. It usually administrated 400 milligrams to 1 gram per kilogram body weight weekly, by which it generally acts as a replacement therapy for many years (Farrugia and Poulis, 2001; Wittstock et al., 2003). Despite the worldwide consumption of IVIg may well above 100 tonnes per year, adverse reactions to IVIg occur in less than five percent of patients (http://consensus.nih.gov/1990/1990IntravenousImmunoglobulin080html.htm), also patients seem to tolerate to IVIg and very few if there is any anti-IVIg responses reported (Lemieux et al., 2005; Imbach, 2012b; Imbach, 2012a). Lack of immunity to IVIg suggests that ingenious designs to harness naturally-occurring configurations inherent in a single antibody-producing B cell could provide a substitute for such approach.

Nevertheless, while foreign antigens, which are molecules derived from a potentially harmful invader, trigger the production of antibodies by the immune system; self antigens such as HMGB1 are usually tolerated by the immune system. In reality, although self antigen-reactive B cells may be present in the body, self antigens are not likely to initiate an immune response and thus without leading to the production of specific antibodies. To effectively transform such challenging circumstances, "site-directed in vitro immunization" (Chin et al., 2007)(U.S. Pat. Nos. 7,494,779, 8,021,860 and 8,158,386) was developed by the inventors to initiate in vitro self antigen-specific immune responses from primary human lymphoid cells. Self antigens can then be neutralized by the resultant mAbs similar to foreign ones.

One of the major problems in obtaining highly potent human therapeutic mAbs is how to isolate antigen-specific clones derived from the site-directed in vitro immunization scheme or even the circulating memory B cell compartment of a human donor. This so-called rare population are clones that under-representative and, accordingly, very little in number. Some of these rare specific cells are expected to be most interesting in modern medicine and thus much research has attempted to address this question, including the use of the antigen-conjugated chitosan as taught by WO 2010104828. However, in light of the limitations of pH-dependent solubility and the reactivity of its amine groups in enzymatic conjugation inherited in biopolymer chitosan to account for many aspects of protein conjugation, it will clearly be important to develop a method for the separation of immune cells by interactions of proteins of said B cells with antigens.

Rabbit antisera have been generated against a synthetic peptide corresponding to the amino terminal part of HMGB1 (amino acid residues 2-15), coupled to radially branching lysine dendrites and against the entire HMGB1 (U.S. Pat. No. 6,468,533). Murine mAbs produced from a hybridoma resulting from the fusion of mouse myeloma with B cells obtained from a mouse immunized with a part of huHMGB1 (amino acid residues 89-1162) or purified recombinant rat HMGB1 (U.S. Pat. No. 7,288,250). Rat mAbs specific to the carboxyl terminal (amino acid residues 200-211) were reported using HMGB1/HMGB2 as an immunogen (Liu et al., 2007). R&D Systems, Inc. makes and sells a polyclonal anti-human HMGB1 antibody (Cat. # AF 1690) produced in chicken immunized with purified, NS0-derived recombinant human HMGB1.

To date, no complete human mAbs with naturally-occurring configurations inherent in a single antibody-producing B cell to HMGB1 neither have the use of such kind of mAbs for inhibiting or treating HMGB1-associated neuromyelitis been reported.

SUMMARY OF THE INVENTION

The object of the present invention is to provide neutralizing antibodies targeting high mobility group box 1 (HMGB1), specifically, the neutralizing antibodies not only containing exclusively human sequences but also comprising naturally-occurring configuration of heavy-and-light-chain combination.

Another object of the present invention is to provide an isolated complete human neutralizing anti-HMGB1 mAbs or antigen-binding portions thereof that bind to HMGB1, preferably the neutralizing epitopes of HMGB1, more preferably the HMG A box and RAGE binding segment of HMGB1. In a preferred embodiment, the neutralizing antibodies are complete human monoclonal antibodies or antigen-binding portions thereof.

Another object of the present invention is to provide a method for producing complete human neutralizing anti-HMGB1 mAbs or antigen-binding portions thereof that binds to at least one part of HMGB1, and the resultant mAbs produced by the method target specific domain of HMGB1 protein with less allergic potential.

Another object of the present invention is to provide a method for inhibiting or treating HMGB1-associated neuromyelitis, comprising administering an effective amount of complete human neutralizing anti-HMGB1 mAbs to a subject in need thereof, the complete human neutralizing anti-HMGB1 mAbs effectively inhibit and/or treat HMGB1-associated neuromyelitis with less allergic responses.

To achieve the objects, the present invention provides an artificial neutralizing antibodies targeting high mobility group box 1 (HMGB1). The artificial neutralizing antibodies is preferably an complete human neutralizing anti-HMGB1 mAbs and produced by the following steps of: (a) providing a synthetic antigen comprising at least one peptide having amino acid sequence represented by SEQ ID NO:3 and SEQ ID NO:4 to immunize a group of human CD56$^-$ lymphocytes; (b) the lymphocytes immunized by the synthetic antigen are enriched by antigen-coupled magnetic beads; (c) adding Epstein-Barr virus (EBV) to the human CD56$^-$ lymphocytes immunized by the synthetic antigen; and (d) selecting the EBV-infected cells that produce the antibodies that recognize HMGB1.

The present invention provides a method for producing an complete human neutralizing anti-HMGB1 mAbs or antigen-binding portions thereof that binds to at least one part of HMGB1, comprising the following steps of: (a) providing a synthetic antigen comprising at least one peptide having amino acid sequence represented by SEQ ID NO:3 and SEQ ID NO:4 to immunize a group of human CD56⁻ lymphocytes; (b) the lymphocytes immunized by the synthetic antigen are enriched by antigen-coupled magnetic beads; (c) adding Epstein-Barr virus (EBV) to the human CD56⁻ lymphocytes immunized by the synthetic antigen; and (d) selecting the EBV-infected cells that produce the antibodies that recognize HMGB1.

In a preferred embodiment of the present invention, in step (b), the lymphocytes immunized by the synthetic antigen are enriched by antigen-coupled magnetic beads by the following steps: (a) His-tagged HMGB1 proteins are immobilized on magnetic beads to form HMGB1-beads complex; (b) mixing the HMGB1-beads complex and the lymphocytes; and (c) releasing the lymphocytes that trapped by the HMGB1-beads complex. Specifically, the "HMGB1 proteins" that immobilized on magnetic beads may be a full-length HMGB1 protein or a specific domain of a HMGB1 protein, such as HMG A box or RAGE binding segment of HMGB1.

In addition, the present invention also provides a method for inhibiting or treating HMGB1-associated neuromyelitis, comprising administering an effective amount of a human monoclonal antibodies to a subject in need thereof, wherein the human monoclonal antibodies are produced by the steps of: (a) providing a synthetic antigen comprising at least one peptide having amino acid sequence represented by SEQ ID NO:3 and SEQ ID NO:4 to immunize a group of human CD56⁻ lymphocytes; (b) the lymphocytes immunized by the synthetic antigen are enriched by antigen-coupled magnetic beads; (c) adding Epstein-Barr virus (EBV) to the human CD56⁻ lymphocytes immunized by the synthetic antigen; and (d) selecting the EBV-infected cells that produce the antibodies that recognize HMGB1.

Other objects, advantages, and novel features of the invention will become more apparent from the following detailed description when taken in conjunction with the accompanying drawings.

DETAILED DESCRIPTION OF THE PREFERRED EMBODIMENT

Prior to describing the invention in further detail, the terms used in this application are defined as follow unless otherwise indicated.

The term "naturally-occurring", as used herein as applied to an object refers to the fact that an object can be found in nature. For example, a combination of heavy and light chain germline immunoglobulins derived from a single human antibody-producing (B) cell that is present in a human that can be isolated from a source in nature, e.g., peripheral blood, and which has not been intentionally modified by man in the laboratory is naturally-occurring.

The term "monoclonal antibody (mAb)" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site (epitope). The modifier "monoclonal" indicates the character of the antibody as being obtained from a substantially homogeneous population of antibodies, and is not to be construed as requiring production of the antibody by any particular method.

The term "complete human antibody", as used herein with regard to an antibody, means that is an antibody not only containing exclusively human sequences but also comprising naturally-occurring configuration of heavy-and-light-chain combination. The antibody is preferably a monoclonal antibody.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period e.g., 8 to 14 days. It will be understood by one of skill in the art that a polypeptide of complete human origin or a polypeptide combination with a naturally-occurring germline configuration typically represents "non-immunogenic in a human".

As used herein, the term "site-directed in vitro immunization" refers to in vitro antigen-specific immune responses from primary human lymphoid cells (Chin et al., 2007)(U.S. Pat. Nos. 7,494,779, 8,021,860 and 8,158,386). This technology relies on presence of coupled T- and B-cell epitopes as well as depleted starting lymphoid populations containing primed precursors recognizing T-cell epitope.

A "heteromyeloma cell line" is a cell line derived from fusion of two different myeloma cells. The two different myeloma cells are preferably a human myeloma cell and a murine myeloma cell. Heteromyeloma cell lines are known in the art. For example, U.S. Pat. No. 6,228,361 and Chin et al., 2001 describe the preparation, characterization and use of various heteromyeloma cell lines.

A "fusion partner" is a cell that can be used to fuse with an antibody-producing cell for a beneficial purpose. Typically, the fusion leads to prolonged antibody production. Thus, without fusion to the fusion partner, the antibody-producing cell ceases to produce antibodies in culture. Upon fusion to the fusion partner, however, fused cells can be selected that produce antibodies in culture for at least about 3 months, preferably at least about 6, 9, 12, 18, 24 months or more. Fusion partners include, but are not limited to, myeloma cells and heteromyeloma cells.

As used herein, the term "antigen-binding region" refers to that portion of an antibody molecule which contains the amino acid residues that interact with an antigen and confer on the antibody its specificity and affinity for the antigen. The antigen-binding region typically comprises the amino acid residues contributed from the paring of the corresponding heavy and light chains necessary to maintain the proper conformation of the antigen-binding residues. The peculiar configuration of specific paring is inherent in a particular antibody-producing B cell.

The term "original (VH/VL) pairing" has been used in the art and herein to illustrate that although a significant number of the available heavy and light chain germline gene segments are used in VH/VL pairing and a given VH sequence can pair with many light chain sequences of both lambda and kappa light chain classes in human Ab generation, the VH/VL pairing is unique in a given B cell survived from peripheral selection. The VH/VL interface between the light chain and heavy chain has been shown to affect the binding kinetics of a peptide (Chatellier et al., 1996), suggesting preference for particular pairings. The interactions between VH/VL contribute significantly to the stability of the antigen-binding region as limited structural changes have significant functional effects on binding affinity. The translation of the human immunoglobulin germline sequences including all known alleles has been provided online such as http://www.imgt.org/.

The present invention is based on the ingenious designs the coupled T- and B-cell epitopes to harness naturally-occurring configurations inherent in a single antibody-producing B cell and simultaneously to isolate antibody-producing B cells with specificity against a self antigen, i.e., HMGB1 (SEQ ID NO:1). It is a very demanding task because of a phenomenon called tolerance; healthy human peripheral lymphoid cells do not normally produce antibodies to self antigens. However, because the site-directed in vitro immunization system utilizes a pre-existing helper T cells derived from tetanus immunization to drive B-cell maturation, several advantages are realized over conventional human mAb strategies. First, the protocol yields antigen-specific B cells rather than antigen-reactive Ig genes, thus eliminating the need of random, non-naturally-occurring recombination required to achieve a detectible Ig binder like in phage display and Ig transgene introduction. Secondly, the rate at which newly formed B cells enter the mature peripheral pool accounts for less than 5% of the immature cells generated in the bone marrow, suggesting a significant selection pressure (Cancro, 2004) and thus a possible mechanism to avoid immunogenicity. The in vivo selection cycles help to circumvent the problems associated with immunogenicity, a process also taken by IVIg to establish a general non-immunogenic status in humans. Third, using an in vitro stimulation scheme, greater than normal antibody repertoire can be obtained from a population of lymphoid cells after antigen exposure. This system is particular useful for the isolation of complete human antibodies against the self antigens.

Culture materials and reagents are known in the art and may be obtained commercially. The culture medium used is RPMI-1640 (HyClone, Logan, Utah), supplemented with 1× non-essential amino acids (Life Technologies, Gaithersburg, Md.), 10% fetal bovine serum (FBS; Life Technologies) and 50 µg/ml of gentamycin and kanamycin (Sinton Chemical & Pharmaceutical, Hsinchu, Taiwan). Purified bovine HMGB1 (Chondrex Inc, Redmond, Wash.) and recombinant human HMGB1 (Sigma, St. Louis, Mo.) are used in antigen-specific and competing enzyme-linked immunosorbent assay (ELISA), together with peroxidase-labeled goat antibodies against human IgG and IgM (Zymed Laboratories, South San Francisco, Calif.) or avidin horseradish peroxidase (eBioscience, San Diego, Calif.) as the reporting system.

Complete human mAbs are produced from in vitro stimulation and culture techniques. Generally, plasma and buffy coat samples from healthy routine blood donors, screened negative for HIV-1/2, HTLV-I/II, HCV, HBsAg and containing normal levels of alanine transferase (ALT), can be obtained from local Blood Centers. Peripheral blood mononuclear cells (PBMC) are isolated by density centrifugation on Ficoll-Paque (GE Healthcare Bio-Sciences, Uppsala, Sweden) as described elsewhere. The resulting PBMC are magnetically labeled with CD45RO MACS® microbeads (Miltenyi) then separated by a VarioMACS™ (Miltenyi) instrument according to the manufacturer's instructions. The purified CD45RO$^+$ T cells are cultured at a density of 2×10$^6$ cells/ml in the culture medium supplemented with 50 µM 2-mercaptoethanol and 10 µg/ml pokeweed mitogen (PWM; Sigma, St. Louis, Mo.). After 24 h, cells are removed by 400×g centrifugation to collect CD45RO$^+$ T cell replacing factor. Removal of cytotoxic cell populations is similarly performed by using colloidal super-paramagnetic microbeads conjugated to monoclonal anti-human CD8 and anti-CD56 antibodies (Miltenyi). Removal of IL-10-producing cells may be achieved by using rat anti-human IL-10 (SouthernBiotech, Birmingham, Ala.) and goat anti-rat IgG microbeads (Miltenyi).

Site-directed in vitro immunization is performed by using cytotoxic cell-depleted PBMC based on a two-step principle. Primary immunization is performed by incubating the cells for 6 days in a medium containing 10 nM of the heterotopic peptide antigen having amino acid sequence represented by SEQ ID NO:5 (QYIKANSKFIGITEL(T-helper epitope of SEQ ID NO:2)-HMG A box (DKARYER-EMKTY) (SEQ ID NO:3); Yao-Hong Biotechnology Inc., New Taipei City, Taiwan) and SEQ ID NO:6 (QYIKAN-SKFIGITEL(T-helper epitope of SEQ ID NO:2)-RAGE binding segment (KDIAAYRAKGKP) (SEQ ID NO:4); Yao-Hong Biotechnology Inc., New Taipei City, Taiwan), 50 µM 2-mercaptoethanol, 10% heat-inactivated human serum, 0.05 ng/ml recombinant human (rh) IL-2 (eBioscience), and 25% (v/v) CD45RO$^+$ T cell replacing factor. For secondary immunization, 3 ×10$^7$ primary-immunized cells are mixed with the peptide in a flask that had been immobilized overnight with 5 mg/ml of CD40L (CD154; eBioscience) together with 1 ×10$^7$ QYIKANSKFIGITEL (Yao-Hong Biotechnology Inc.)-stimulated CD4$^+$ T cells and 5 ng/ml rh IL-15 (eBioscience). The cells are cultured for 3-5 days in a medium supplemented with 5% human serum, 50 mM 2-mercaptoethanol and 10 nM heterotopic peptide antigens.

The concept of using immobilized-metal affinity chromatography (IMAC) to fractionate or purify proteins has first been formulated and its feasibility shown by Porath et al. in 1975. The idea was based on the known affinity of transition metal ions such as $Zn^{2+}$, $Cu^{2+}$, $Ni^{2+}$, and $Co^{2+}$ to histidine and then strongly fixed metal ions to a support for fractionating protein containing such an amino acid (His-tag). The chelating reagents used to fix the metal to a solid support are commercially available and usually involve a tridentate chelator iminodiacetic acid (IDA), tetradentate chelators nitrilotriacetic acid (NTA) and carboxymethyl aspartate (CM-Asp). Bound proteins can be eluted and thus fractionated or purified in four following ways: (1) lower the pH; (2) add excess imidazole; (3) add EDTA to remove metal ion from purification resin and/or (4) add enzymes to cleave His-tag (Gaberc-Porekar and Menart, 2005). It is now well established that IMAC is a highly efficient procedure to purify His-tagged proteins; in fact, recombinant proteins are artificially terminally labeled with His tags in a form of oligo-His to serve as an affinity handle for the ease of subsequent purification because naturally occurring proteins are lack of stretches of continuous His residues. Therefore, unlike biopolymer chitosan which depends on pH and amine groups for conjugation, virtually any protein can be purified from a cell extract in just one or two steps. In one embodiment, the present invention provides a novel method for the separation of specific B cells by interactions of proteins of said immune cells with antigens. Typically, the His-tagged HMGB1 proteins (Sino Biological, Beijing, China) are immobilized on $NTA^-$ $Ni^{2+}$ magnetic nanobeads (Taiwan Advanced Nanotech, Taoyuan, Taiwan) and the HMGB1-nanobeads complex is immersed to trap the immune B cells to the complex. Specific B cells retained on a magnetic field were then released by citric acid-$Na_2HPO_4$ buffer containing 1 U/ml thrombin, 1 mM EDTA and 500 mM imidazole (Sigma).

Subsequently, the in vitro immunized cells are infected with Epstein-Barr virus (EBV) by virus-containing supernatant derived from the EBV-producing marmoset cell line B95-8 (American Type Culture Collection, ATCC CRL 1612). The infected cells are seeded at $10^5$/well in 96-well plates together with mytomycin (Kyowa Hakko Kogyo, Tokyo, Japan)-treated PBMC as feeder cells ($10^4$/well) for the establishment of lymphoblastoid cells and screened for Ab production by ELISA. HMGB1-specific ELISA can be performed by coating 0.25 µg/ml purified HMGB1, 1 µg/ml bovine serum albumin (BSA; Sigma) or 1 µg/ml tetanus toxoid (TT; ADlmmune, Taichung, Taiwan) onto microtitre plates overnight at 4° C. Culture supernatants are diluted to the desired level in 10 mM sodium phosphate buffer (pH 8.0), containing 0.5 M sodium chloride and 0.1% Tween-20. Coated plates are incubated with diluted culture supernatants, washed, incubated with peroxidase-labeled goat antibodies against human IgG and IgM and developed (15 min) by addition of 100 µl of the chromogenic substrate o-phenylaenediamine (OPD) (Sigma). The reaction is stopped after 30 min by adding 1 M sulphuric acid, and the absorbances are read at 490 nm.

Somatic cell hybridization can be further applied to optimize human antibody and can be generated by electrofusion. Briefly, HMGB1-specific EBV-infected lymphoblastoid cells were fused with heteromyeloma cells (Chin et al., 2001) in an isotonic medium (280 mM sorbitol, 0.5 mM magnesium acetate, 0.1 mM calcium acetate and 1 mg/ml BSA; pH6.9-7.1). Cell fusion can be induced by high-voltage pulses using a BTX Electro Cell Manipulator ECM 2001 (Harvard Apparatus, Holliston, Mass.). HMGB1-specific hybrids were selected and cloned by limiting dilution.

Methods for determining whether an antibody or antigen-binding fragment inhibits a HMGB1-induced pro-inflammatory condition are known to one skilled in the art. For example, inhibition of the release of an inflammatory cytokine from a cell in culture can be measured accordingly. For example, as described and exemplified herein, TNF release from human monocytic populations can be measured using $CD14^+$ cells sorted magnetically with MACS® microbeads (Miltenyi). TNF that is released from the monocytes is measured by a commercial kit obtained from R & D Systems (Minneapolis, Minn.). Methods for measuring release of other related cytokines from cells are also known in the art.

Assays to determine affinity and specificity of binding are known in the art, including competitive and non-competitive assays. A competitive assay is preferred in this analysis. The affinity of the mAb can be determined against HMGB1 protein with an AffinixQN quartz crystal microbalance (QCM) biosensor (Inishiamu Inc., Tokyo, Japan) according to the manufacturer's instructions. Different amounts of synthetic peptides can then be incorporated into the reaction for competition to confirm the specificity of human mAbs.

The exact pathogenic process to neuropathic diseases is currently unknown, but experimental autoimmune/allergic encephalomyelitis (EAE) is primarily used as an animal model of autoimmune inflammatory diseases of the CNS and in many aspects resembles human neuropathic diseases, such as MS and NMO. This demyelinating model can be used to evaluate the effectiveness of human mAbs in alleviating diseases and is known to one skilled in the art. Immunization with myelin oligodendrocyte glycoprotein (MOG) induces a chronic form of EAE. Different amounts of synthetic peptides can then be incorporated into the reaction for competition to confirm the specificity of human mAbs. Human mAbs can then be incorporated into the system for verifying the tendency to resolve inflammation and demyelination.

The following examples are offered to illustrate this invention and are not to be construed in any way as limiting the scope of the present invention.

EXAMPLES

Example 1

Specificity of Hybrids Cell Line

Figure 1:
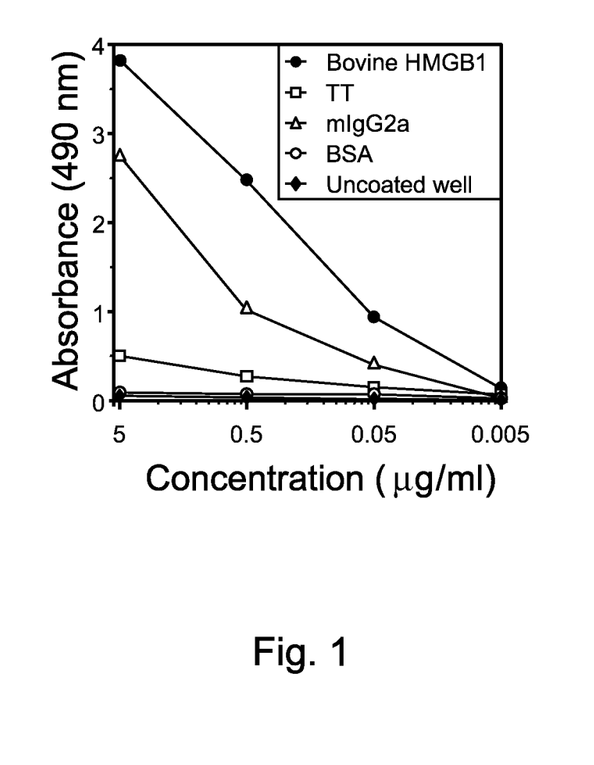
FIG. 1 illustrates a representative ELISA reactivity profile of culture supernatant. Diluted supernatants were tested in duplicate with 100 μL added to each well. Deviation between duplicate was less than 10% for any reported value.

Ag-specific enzyme-linked immunosorbent assay (ELISA) was performed by coating 1 µg/ml purified bovine HMGB1, 1 µg/ml recombinant human HMGB1, 1 µg/ml bovine serum albumin (BSA; Sigma) or 1 µg/ml tetanus toxoid (TT; ADlmmune, Taichung, Taiwan) onto microtitre plates overnight at 4° C. Culture supernatants were diluted to the desired level in 10 mM sodium phosphate buffer (pH 8.0), containing 0.5 M sodium chloride and 0.1% Tween-20. Coated plates were incubated with diluted culture supernatants from the cell line, washed, incubated with peroxidase-labeled goat antibodies against human IgG and IgM and developed (15 min) by addition of 100 µl of the chromogenic substrate o-phenylaenediamine (OPD) (Sigma). The reaction was stopped after 30 min by adding 1 M sulphuric acid, and the absorbances were read at 490 nm (FIG. 1).

Example 2

Inhibition of TNF Release by Anti-HMGB1 Monoclonal Antibodies

Figure 2:
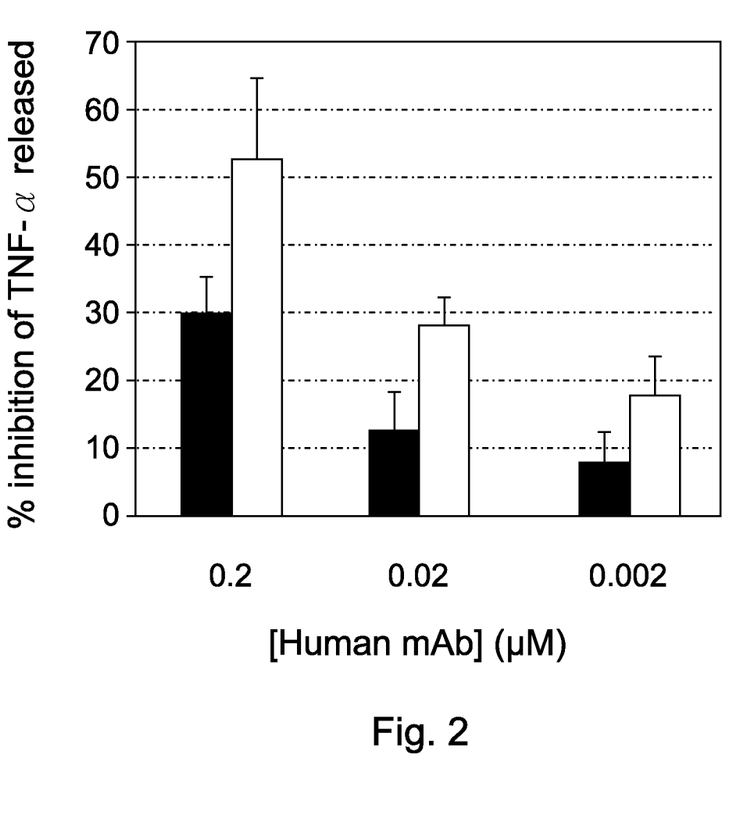
FIG. 2 is a histogram depicting the representing results of HMGB1 neutralizing experiments of two human mAbs. Human TNF was induced by stimulating monocytes with 1 μg/ml of bovine HMGB1. Purified HMGB1 monoclonal antibodies were added to give a final concentration of 10%.

The ability of particular human mAbs to inhibit HMGB1-induced TNF release was assessed in human primary monocytes administered only HMGB1, HMGB1 plus particular HMGB1 mAbs, or an isotype control antibody. Freshly purified human monocytes cultures were stimulated with 1 µg/ml purified bovine HMGB1 and culture supernatant were sampled four hours later to be assayed for TNF. As depicted in FIG. 2, two particular human mAbs inhibited TNF release, indicating that such antibodies could be used to neutralize the biological activity of HMGB1 and thus for alleviating neuropathic diseases.

Example 3

Completion of mAb Binding to HMGB1 by the Immunogen

Figure 3:
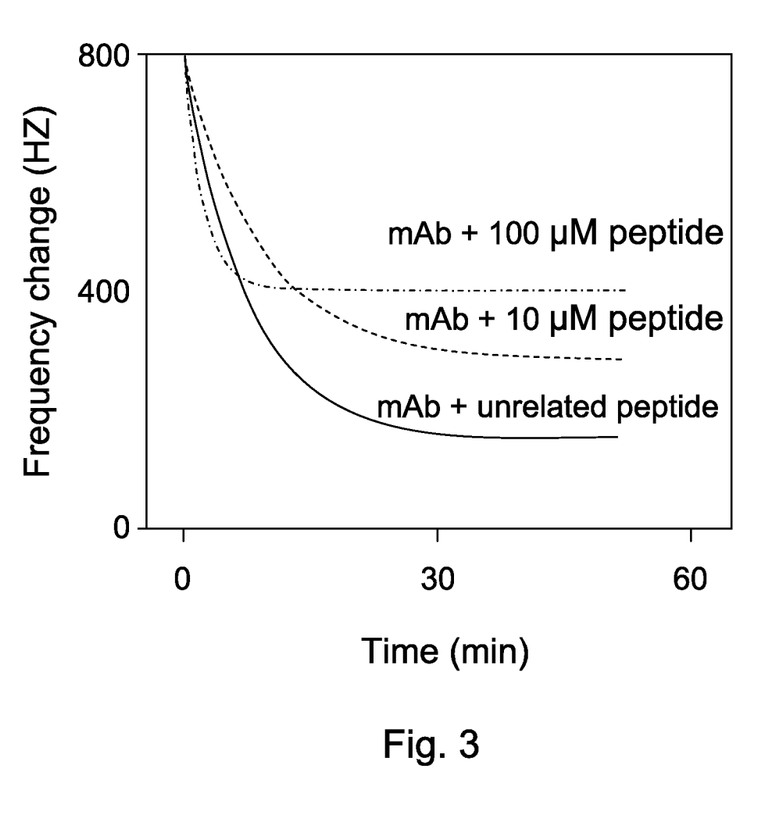
FIG. 3 shows specific antigen-antibody reaction was detected on the surface of a QCM chip. Real-time monitoring of protease reaction denoted that competition was observed when the peptide used containing the immunogen sequence but not amino acid composition-compatible peptide, indicating the specificity of mAb towards the corresponding immunogen.

As shown in FIG. 3, QCM was used to perform kinetic analysis of interaction between HMGB1, a representing mAb and peptides with the same amino composition. HMGB1 was injected to saturate the chip. The frequency change of mAb with immunogen-containing peptide or an irrelevant peptide with the same amino composition was analyzed by Aqua™ software. The results indicated that the mAb binding to HMGB1 can be only replaced by the immunogen-containing peptide.

Example 4

HMGB1 Neutralization In Vivo

Figure 4:
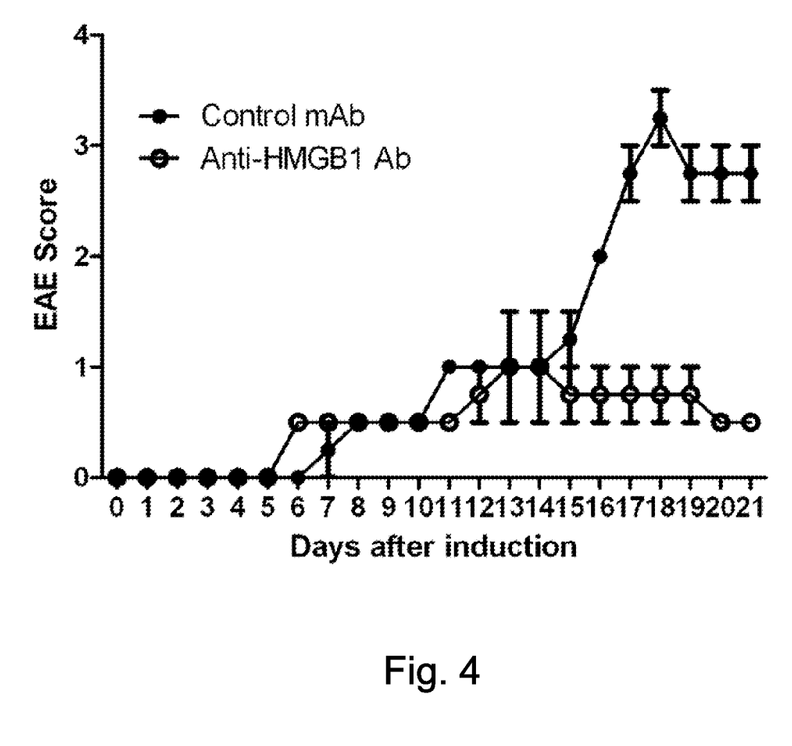
FIG. 4 denotes anti-HMGB1 contributes to EAE alleviation in experimental animals. Data are representative of two experiments of ≥5 mice per group.

Chronic experimental allergic encephalomyelitis (EAE), which represents an animal model of human neuromyelitis, was induced in C57BL/6 mice by immunization with an emulsion of MOG35-55 or MOG1-125 in complete Freund's adjuvant (CFA) distributed in three spots on the flank, followed by administration of pertussis toxin (PTX) in PBS, first on the day of immunization and then again the following day. EAE is scored on scale 0 to 5, based from no obvious changes in motor function compared to non-immunized mice to mice spontaneously rolling in the cage, respectively. 100 μg of purified anti-HMGB1 antibody or isotype control antibody was injected intraperitoneally at days 5 and 7 post MOG injection. From day 15, Human anti-HMGB1 mAb demonstrated significant alleviating effect (FIG. 4).

Although the present invention has been explained in relation to its preferred embodiment, it is to be understood that many other possible modifications and variations can be made without departing from the spirit and scope of the invention as hereinafter claimed.

What is claimed is:

1. A method for producing human monoclonal antibodies that binds to at least one part of HMGB1, comprising the following steps of:
    (a) providing a synthetic antigen consisting of T-helper epitope SEQ ID NO: 2 coupled to SEQ ID NO: 4 to immunize a group of human CD56⁻ lymphocytes;
    (b) the lymphocytes immunized by the synthetic antigen are enriched by antigen-coupled magnetic beads;
    (c) adding Epstein-Barr virus (EBV) to the human CD56⁻ lymphocytes immunized by the synthetic antigen; and
    (d) selecting the EBV-infected cells that produce the antibodies that recognize HMGB1.

* * * * *